(12) United States Patent
Federsel et al.

(10) Patent No.: US 6,414,141 B1
(45) Date of Patent: Jul. 2, 2002

(54) PROCESS FOR PURIFYING AN AMPICILLIN PRO-DRUG ESTER

(75) Inventors: Hans-Jürgen Federsel, Bromma; Erik Könberg, Älvsjö, both of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/230,476

(22) PCT Filed: Dec. 17, 1998

(86) PCT No.: PCT/SE98/02347

§ 371 (c)(1),
(2), (4) Date: Jan. 26, 1999

(87) PCT Pub. No.: WO99/32493

PCT Pub. Date: Jul. 1, 1999

(30) Foreign Application Priority Data

Dec. 22, 1997 (SE) ................................. 9704868
Jan. 29, 1998 (SE) ................................. 9800255

(51) Int. Cl.[7] .............................................. C07D 499/18
(52) U.S. Cl. ........................................ 540/324; 540/336
(58) Field of Search ................................ 540/318, 324, 540/336

(56) References Cited

U.S. PATENT DOCUMENTS 4,889,929 A * 12/1989 Vaya et al. ................. 540/318

FOREIGN PATENT DOCUMENTS

| EP | 0004740 | 10/1979 |
| EP | 0273156 | 7/1988 |
| GB | 1382409 | 1/1975 |
| SE | 78101227 | 9/1978 |

OTHER PUBLICATIONS

Sybil P. Parker, ed., McGraw–Hill Dictionary of Scientific and Technical Terms, 5th ed., New York, p. 449.*

* cited by examiner

*Primary Examiner*—Richard L. Raymond
*Assistant Examiner*—Thomas McKenzie
(74) *Attorney, Agent, or Firm*—White & Case LLP

(57) ABSTRACT

Applicants have developed a process for purifying an ampicillin pro-drug ester, e.g., bacampicillin, or an acid addition salt thereof of formula I.

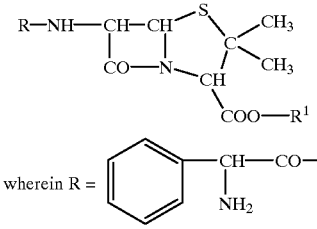

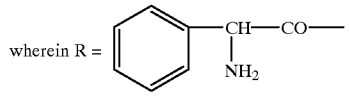

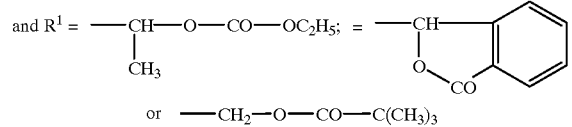

The process comprises a step wherein a crude solution of the pro-drug ester is subjected to an evaporation which is controlled by the evaporation rate of the organic solvent such that a continuous operation is accomplished for the crystallization of the desired purified pro-drug ester or salt thereof. Said crystallization is preferably preceded by an aqueous phase extraction and/or an organic phase extraction, both preferably also being performed continuously.

35 Claims, 1 Drawing Sheet

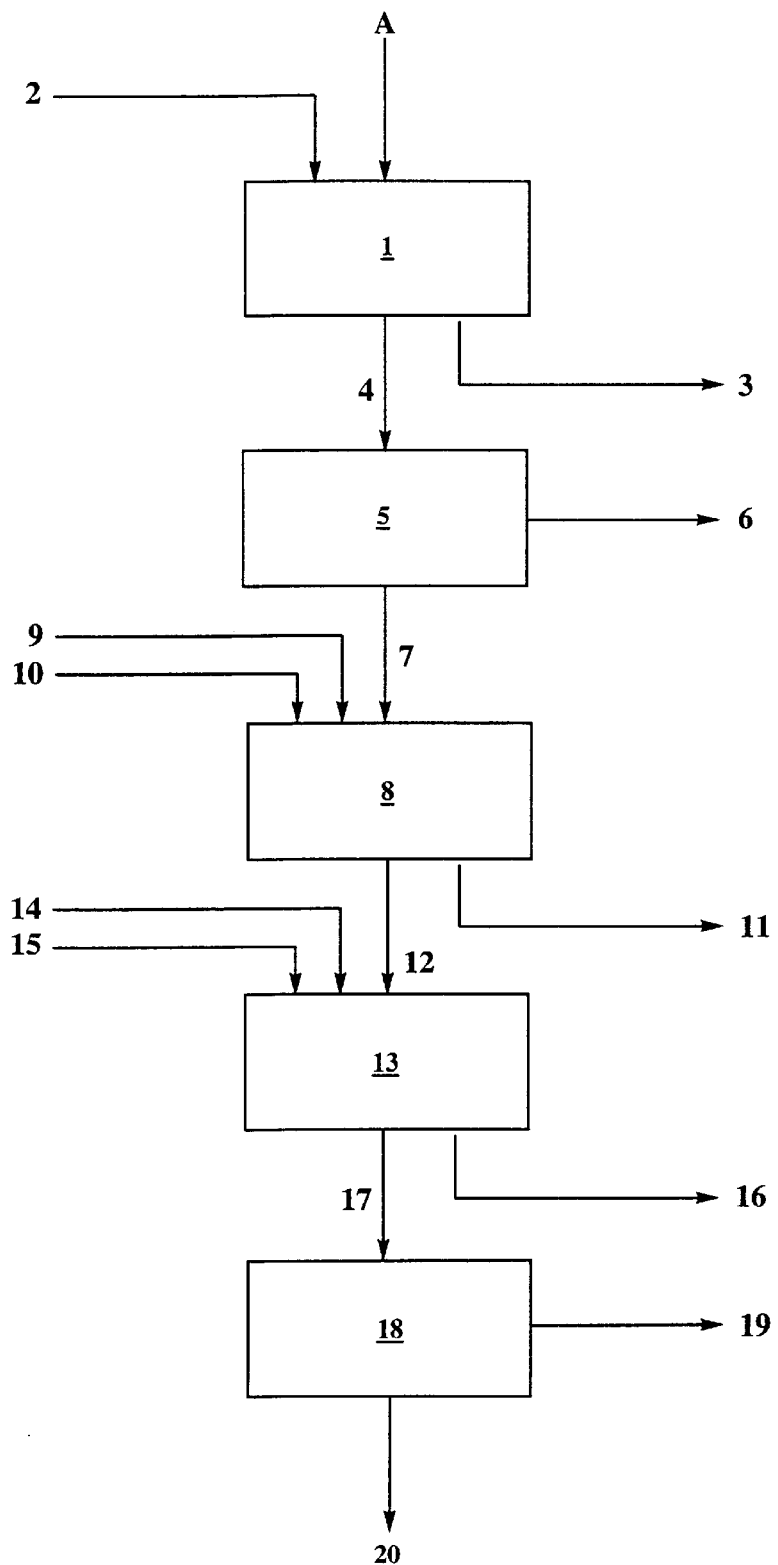
Figure

PROCESS FOR PURIFYING AN AMPICILLIN PRO-DRUG ESTER

This application is the National Stage of International Application No. PCT/SE98/02347, filed Dec. 17, 1998.

TECHNICAL FIELD

The present invention relates to a novel and improved process for purifying a solution of an ampicillin pro-drug ester from contaminants originating from the manufacture thereof. The novel process is of special value in connection with the removal of basic components used to neutralize acidic ones liberated in the synthesis of the ampicillin pro-drug ester referred to.

BACKGROUND OF THE INVENTION

One of the commercially important ampicillin pro-drug esters is bacampicillin, or a salt thereof, such as bacampicillin hydrochloride. The final step in the manufacture thereof can generally be represented by the following reaction scheme:

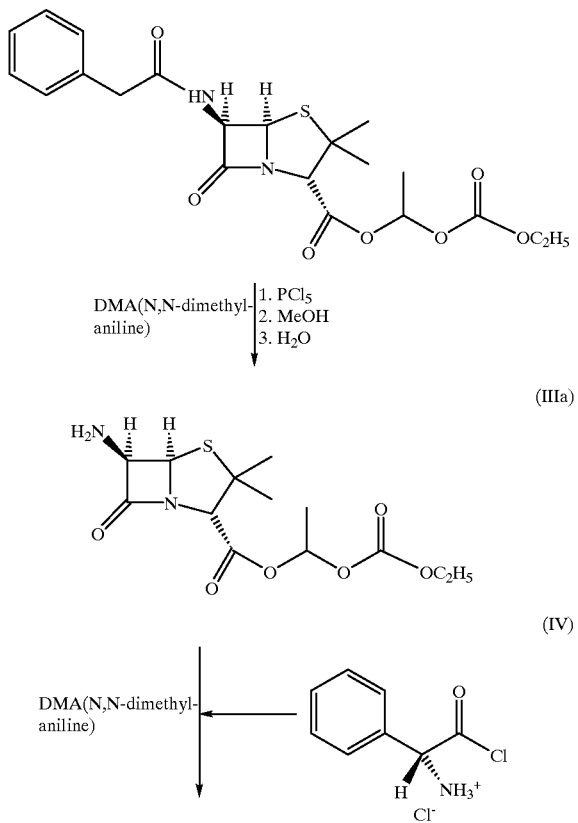

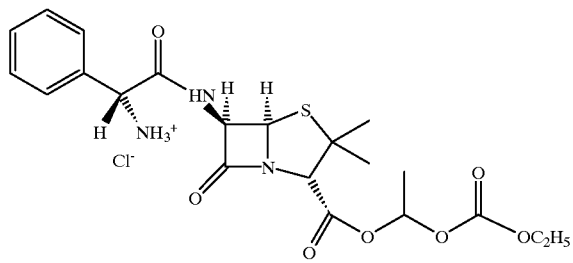

Thus, the penicillin G ester II is reacted with phosphorous pentachloride at low temperature followed by an alcohol, e.g. methanol, and water, and the 1'-ethoxycarbonyloxyethyl ester of 6-aminopenicillanic acid (6APA) formed thereby (formula IIIa) is then reacted with phenylglycine chloride hydrochloride (formula IV) under such conditions that bacampicillin hydrochloride of formula Ia is formed. Said conditions involve the presence of DMA (N,N-dimethylaniline) or other bases to bind the hydrochloric acid liberated in the reaction. If said base is not efficiently removed in the isolation of bacampicillin hydrochloride, it will contaminate the final product to be used in a pharmaceutical preparation. Moreover, since DMA has proven to possess potential health hazards, it is necessary to eliminate said contaminant to as great an extent as possible.

In spite of the availability of several purification techniques which may seem efficient when used alone in other connections, it has, however, not previously been possible in practice to develop a process which fulfills the requirements. Apart from being inadequate as far as the purity of the end product is concerned, such techniques have also involved some inactivation of said esters.

One method of improving the purification operation is disclosed in Swedish patent No. 7810122-7, which discloses a method of removing DMA from some ampicillin pro-drug esters by means of a step wherein a specific cation exchanger is utilized.

The present invention is based on a simple and very efficient alternative to said ion exchange resin operation, which has been shown to result in improved yields as well as higher purity of the desired end product, in spite of the fact that the novel process claimed involves a crystallization operation, against which there was a prejudice in the prior art.

BRIEF DESCRIPTION OF THE DRAWING

The FIGURE is a schematic flow sheet of an embodiment of the inventive process for purifying ampicillin pro-drug esters.

GENERAL DESCRIPTION OF THE INVENTION

The present invention is based on the discovery that it is possible to perform, on a commercial scale and in a simple and efficient way, a continuous crystallization operation on a crude organic solution of the type referred to above of an ampicillin pro-drug ester. This is indeed unexpected as the organic phase which is taken to the crystallization operation is unstable, which means that a crystallization operation would have been expected to result in an inoperable and/or inferior process.

According to the present invention, however, it has been found possible to subject the organic crude solution to an evaporation that results in a continuous crystallization of the desired product, viz. by controlling the evaporation rate of the organic solvent properly to achieve said continuous crystallization. By this means the desired end product is obtained in very good yield and in a highly purified state. Furthermore, the product obtained by the purification process according to the invention is of a very homogeneous quality, which is also easy to centrifuge and is not inactivated by the crystallization operation.

More specifically, a first aspect of the invention relates to a process for purifying a solution of an ampicillin pro-drug ester of formula I:

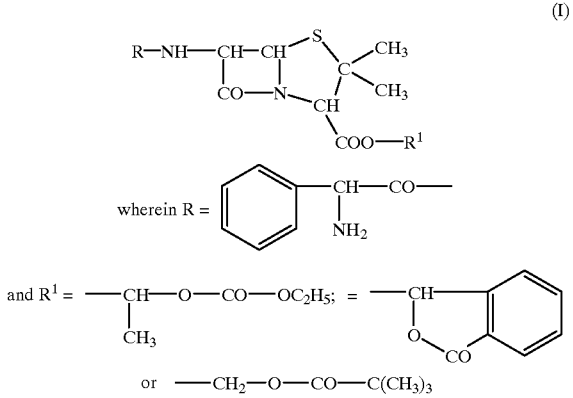

or acid addition salts thereof;

from contaminants originating from the manufacture thereof, especially to remove base used when incorporating the R group into said ester of formula I, such as from the corresponding ester wherein R is phenylacetyl ($PhCH_2CO$), which comprises a step wherein a crude solution of said ampicillin pro-drug ester of formula I, or an acid addition salt thereof, in an organic solvent therefor, is subjected to an evaporation which is controlled by the evaporation rate of the organic solvent such that a continuous operation is accomplished for the crystallization of the desired purified pro-drug ester, or salt thereof.

In other words the process is generally applicable to the purification of bacampicillin, talampicillin and pivampicillin, or acid addition salts thereof, for instance the hydrochloride salts thereof. According to an especially preferred embodiment of the invention the process is adapted to the purification of bacampicillin, or an acid addition salt thereof, preferably the hydrochloride salt.

The ampicillin pro-drug ester to be purified by the process claimed is generally manufactured starting from penicillin G, or a salt thereof, especially the potassium salt, which is reacted with a reagent $R^1$—X, wherein $R^1$ is as defined in connection with formula (I) and X is halogen, with the formation of a penicillin G ester, the ester group being R as defined above. Said ester is then reacted with phosphorus pentachloride at low temperature followed by an alcohol, for example methanol, and water, and then with a reagent R—Y, wherein R is as defined in connection with formula (I) and Y is halogen, under such conditions that the phenylacetyl group is replaced by the group R. In said reaction an organic base, such as N,N-dimethyl aniline, is used, as was mentioned in the opening part of the present description, and said organic base is thus one of the major impurities to be removed from the ampicillin pro-drug ester subsequently used for medical purposes. However, by more preferable embodiments of the process substantially all contaminants originating from the whole manufacturing process can be removed or at least substantially eliminated. Details about the full manufacturing process and contaminants in connection therewith can be found in technical literature within this field, as said manufacturing process is previously known per se and is not part of the present invention.

As was referred to above the invention is primarily based on the idea of performing a continuous crystallization operation, a number of advantages thereby being accomplished. Such continuous crystallization is operable by proper control of the evaporation rate of the organic solvent. In this context it is not possible to define said control in exact specific figures, but now that the inventive idea has been disclosed, proper control conditions could be easily established by a person skilled in the art in each specific case. Preferably, however, the evaporation rate could generally be defined such that the continuous crystallization is performed at an evaporation rate corresponding to 0.1–0.6 times the continuously added volume of solution to be purified, per hour. More preferably said evaporation rate corresponds to 0.3–0.5, even more preferably about 0.4, times said volume, per hour.

The continuous crystallization operation is preferably performed in vacuo, i.e. at a sub-atmospheric pressure, primarily because the temperatures to be involved therein will be sufficiently low not to decompose the desired product or deteriorate the same in any way.

Generally the temperatures used in the continuous crystallization operation are at a level where decomposition or deterioration of the desired product is avoided. As is well known they are also dependent on the pressure utilized in the operation. A preferred temperature range is, however, generally 25–75° C., more preferably 25–50° C. For cost and investment capital reasons, as well as product quality reasons, an especially preferable temperature range, in particular when the operation is performed in vacuo, is however such a low temperature range as 25–35° C., especially around 30° C.

The main purpose of the continuous crystallization operation is, as was mentioned above, to remove or substantially eliminate the base referred to, e.g. DMA, but as the process for the manufacture of the starting crude ester solution involves the use of several different reagents, many other contaminants should also be removed in order to obtain a high quality ampicillin pro-drug ester. Furthermore, outstanding results of the crystallization operation, or the total process as described more in detail below, are accomplished by such further operations as they generally also involve the removal of major quantities of DMA, or other bases, before said crystallization reaction is performed.

According to one preferable embodiment of the process claimed this involves a step preceding the continuous crystallization wherein other contaminants, more specifically polar contaminants, are removed from the solution to be purified by subjecting the same to an extraction with an aqueous phase.

An especially preferable embodiment in this respect is represented by a case wherein said aqueous phase extraction step is performed continuously. By a continuous extraction of this kind it has been found possible to reduce the level of polar contaminants to an extremely low value as compared to a case where an extraction in a batch-wise manner is performed. Moreover, in a process of this type one single batch-wise extraction only is possible as the different phases are not separable a second or third time but merely once.

An extremely efficient extraction in this respect is accomplished in accordance with the invention if said continuous extraction step is performed in a counter current flow column, a strainer column being especially preferred.

The volume flow ratio of organic solution to be purified to aqueous extraction phase is preferably within the range of from 2:1 to 1:2, most preferably around 1:1.

The extraction efficiency in this embodiment is extremely high if water containing an inorganic acid salt is used in order to accomplish the proper density difference as well as a sufficiently rapid separation of the phases involved. Although many metal salts can be used in this respect, an alkali metal salt, preferably a halide of an alkali metal, is generally utilized. Especially a chloride salt is used, such as sodium chloride.

Efficient extraction is achieved by means of an aqueous medium containing 5–30%, preferably 5–20%, more preferably 8–18% (w/w), of said salt.

The pH to be used in said aqueous phase extraction step is suitably controlled within the range of 2–5, preferably 3–4, more preferably 3.4–3.7.

According to another preferable embodiment of the process according to the invention, the continuous crystallization operation is preceded by a step wherein organic contaminants also removed, viz. by an extraction with an organic phase. The organic solvent used in the organic phase extraction step is any solvent having the ability of removing the desired organic contaminants but is preferably selected from butyl acetate, methyl isobutyl ketone and ethyl acetate, butyl acetate being especially preferred.

As should be understandable from the above, the most interesting aspect of the process claimed is represented by an operation wherein the aqueous phase extraction as well as the organic phase extraction are both utilized before the crystallization operation, all of said steps preferably being performed continuously. In this connection an advantageous embodiment of the invention means that said aqueous phase extraction precedes said organic phase extraction.

Furthermore, the different steps of the total process are preferably arranged such that the aqueous phase which leaves the organic phase extraction operation, with the desired product enriched therein, is subjected to a salting-out extraction step wherein the desired product to be subsequently crystallized is transferred from said aqueous phase into a new organic phase. Said new organic phase, with desired product enriched therein is then passed to the continuous crystallization operation step.

It is important that the organic phase is formed in the correct way in order to achieve the most successful result of the subsequent crystallization operation. Thus, the organic solution containing the product to be crystallized in the continuous crystallization operation is supersaturated and crystallization starts at a very early stage. By the new technique according to the present invention the "salting-out" extraction does not result in any phase separation problems or any substantial losses of desired end product in the aqueous phase, as was the case in connection with prior art techniques. Furthermore, the "salting-out" extraction step facilitates the subsequent crystallization operation and makes the last-mentioned operation much more efficient.

The salting-out extraction step referred to is also preferably performed in a continuous manner. The term "salting-out" extraction step originates from the fact that said step is preferably performed in the presence of a salt, e.g. an inorganic salt, causes the salt of the desired pro-drug ester to be transferred from the aqueous phase into the new organic phase. The purpose of said salt is to change the distribution coefficient between the two phases and the use of any other "phase-transfer" agent than a salt to improve said transfer is also within the scope of the invention. However, a preferable salt in this respect is a metal salt of an inorganic acid, especially in the form of an aqueous solution thereof. Many metal salts are useful but an alkali metal salt, e.g. from sodium, is preferred. A halide salt is especially preferred, such as a chloride salt, e.g. sodium chloride. Furthermore, it has been found especially preferable to utilize a saturated water solution of the salt referred to.

The organic solvent to be used for the salting-out extraction step is generally chosen while taking into account the ability of dissolving the desired product as well as of crystallizing said product in the subsequent crystallization operation. However, preferably it is selected from butyl acetate, methyl isobutyl ketone, dichloromethane and ethyl acetate, butyl acetate being especially preferred.

One advantageous embodiment of the invention in this respect is represented by the case where the flow volume ratio of pro-drug ester solution:salt solution:organic solvent is within the range of 1.0–1.5:1.5–2.0:1, especially 1.3:1.6:1.

Still another advantageous embodiment of the process claimed encompasses an evaporation step between said aqueous phase extraction step and said organic phase extraction step, to evaporate organic solvent from the product-containing organic phase which leaves said aqueous phase extraction, which organic solvent is then replaced by another organic solvent to be used in the organic phase extraction for the extractions of organic contaminants therein.

Such an evaporation step enables a proper control of the organic contaminants to be removed. That is, by proper choice of the replacement solvent the contamination removal efficiency can be tailored for the specific process used. Preferable replacement organic solvents are those solvents which were referred to above in connection with the organic phase extraction.

According to another aspect of the invention a novel process for purifying a solution of an ampicillin pro-drug ester of formula I, or acid addition salts thereof, from contaminants referred to above is provided which comprises a step wherein a crude solution of said ester or salt is subjected to an extraction with an aqueous phase to remove polar contaminants therefrom, said extraction being performed in a continuous operation.

That is, irrespective of whether any of the other steps referred to above are performed or not, this represents a novel and advantageous technique in this field, which per se is non-obvious and gives unexpected results, inter alia for the reasons stated above.

Generally said continuous extraction is performed in a counter current flow column, preferably a strainer column, and preferably also with an aqueous medium containing an inorganic acid salt, the details concerning such salts being the same as those disclosed above.

As to other preferable embodiments of this aspect of the invention, reference is made to those preferable embodiments which were presented above in connection with the aqueous phase extraction step. Thus, such embodiments need not be repeated here.

In said second aspect of the invention the aqueous phase extraction can also be followed by an organic phase extraction and/or evaporation step and/or salting-out extraction step and/or continuous crystallization operation as defined above, all preferable embodiments of last-mentioned two steps being the same as those preferable embodiments which were described above.

As can also be gathered from the above, one advantageous application of the processes claimed relates to the case where the crude starting solution has been manufactured by incorporating the group R in formula I in the 6-APA-ester of formula III:

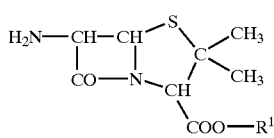

(III)

wherein $R^1$ is as defined above, in the presence of a base, especially N,N-dimethylaniline, R preferably being incorporated by means of a phenylglycine halide, especially the chloride, or the hydrochloride thereof, as a reactant.

According to one interesting embodiment of the invention the ampicillin pro-drug ester to be purified is bacampicillin or an acid addition salt thereof, preferably the hydrochloride thereof.

The purified end product as obtained from the continuous crystallization operation is finally subjected to conventional recovery operations, such as centrifugation, drying, etc., which need not be described more in detail here.

FIGURE

The process according to the invention will be further exemplified by means of the FIGURE and the Examples below, said illustrations being of a non-limiting nature.

The FIGURE shown is a schematic flow sheet of one embodiment of the new process according to the invention.

This flow sheet shows a process where a crude solution of the ampicillin pro-drug ester to be purified, generally designated A, is passed to a first extraction operation 1, which is performed as an aqueous phase extraction. More specifically, the polar contaminants are extracted from said crude solution A by means of a water phase 2 which is discarded as water phase 3.

The organic phase 4 which leaves said first extraction operation 1 is then passed to an evaporation step 5 from which organic solvent is withdrawn via 6 and the residue 7 is passed to an organic phase extraction 8. To said organic phase extraction 8 a new organic solvent as well as water are added via lines 9 and 10, respectively.

The organic contaminants are then discarded in the organic phase 11, while the water phase 12 from last-mentioned extraction is passed to a salting-out extraction 13 performed in the presence of an organic solvent as well as a saturated aqueous salt solution added via lines 14 and 15, respectively.

The water phase 16 from said salting-out extraction is discarded while the organic phase 17 therefrom is passed to a crystallization operation 18. From said operation 18 there are obtained an organic solvent 19 and the desired crystallized product 20 which can then be recovered in any conventional manner.

In the embodiment shown all steps are performed in a continuous manner as previously described.

EXAMPLE 1

Synthesis and purification of bacampicillin 1'-ethoxycarbonyloxyethyl 6-(Dα-aminophenylacetamido) penicillanate hydrochloride.

N,N-dimethylaniline (36.3 g, 0.30 mol) was added to a stirred solution of 1'-ethoxycarbonyloxyethyl6-(phenylacetamido)pencillanate 54 g, 0.12 mol) in dichloromethane (420 ml) at −45° C. While maintaining the temperature at −45° C., phosphorus pentachloride (29.7 g, 0 142 mol) was added in 5 equal portions at intervals of 6 minutes. 45 minutes after the last addition, methanol (49.7 g, 1.55 mol) was added dropwise to the mixture during 45 minutes at such a speed that the temperature did not exceed −24° C. After a stirring period of 30 minutes, water (26.8 g, 1.49 mol) was added during 15 minutes, and the temperature was adjusted to −45° C. and N,N-dimethylaniline (64.7 g, 0.535 mol) was added followed by D-α-phenylglycine chloride hydrochloride (25.6 g, 0.124 mol).

The mixture was diluted with 70 ml of dichloromethane and 7 g of hydrochloric acid were added, and the solution obtained was extracted in a counter current flow extraction column with diluted saline as the aqueous phase. The dichloromethane phase was evaporated and the residue was partitioned between butyl acetate (255 ml) and water (580 ml) after a pH-adjustment with sodium bicarbonate to a pH ~3. The aqueous phase was washed with butyl acetate (100 ml) and the combined organic phases were extracted with water (120 ml).

The combined aqueous phases were continuously admixed with a saturated sodium chloride solution (760 ml) and butyl acetate (480 ml) and were then continuously separated. The organic phase was continuously evaporated during the desalting operation in vacuo at a bath temperature of 40–45° C., whereupon-the product started to crystallize. After about 4 hours at room temperature the product was filtered and washed with 190 ml of butyl acetate and 190 ml of ethyl acetate. The damp substance was dried at 50–60° C. and white to yellowish crystals were obtained (47 g; 78% yield based on the penicillin G ester).

The N,N-dimethylaniline contamination was <10 ppm, according to GC-analysis.

EXAMPLE 2

Comparative Example

Synthesis and purification of bacampicillin 1'-ethoxycarbonyloxyethyl 6-(D-α-aminophenylacetamido) penicillanate hydrochloride N,N-dimethylaniline (31 g, 0.256 mol) was added to a stirred solution of 1'-ethoxycarbonyloxyethyl 6-(phenylacetamido)penicillanate (54 g, 0.12 mol) in dichloromethane (440 ml) at −35° C. While maintaining the temperature at −35° C., phosphorous pentachloride (27.6 g, 0.132 mol) was added in 5 equal portions at intervals of 6 minutes. 6 minutes after the last addition methanol (24 g, 0.75 mol) was added dropwise to the mixture at such a rate that the temperature did not exceed −20° C. Then water (21.6 g, 1.2 mol) was added during 10 minutes, and the temperature was adjusted to −35° C. and N,N-dimethylaniline (62.2 g, 0.514 mol) was added followed by D-α-phenylglycine chloride hydrochloride (27.2 g, 0.132 mol). The mixture was stirred for 1 hour, the temperature rising to −23° C. during said period. Then the mixture was poured into a solution of sodium bicarbonate (8.2 g) in 360 ml of water.

After a stirring period of a few minutes the aqueous phase was separated and extracted with 200 ml of dichloromethane. The organic phases were combined, and dissolved substances were removed from the solvent and the residue was partitioned between methyl isobutyl ketone (240 ml) and water (600 ml). The aqueous phase was washed with butyl acetate (100 ml) and the combined organic phases were extracted with water (60 ml).

The combined aqueous phases were stirred for a few minutes with sodium chloride (130 g) and butyl acetate (320 ml). After the separation the aqueous layer was extracted once more with butyl acetate (160 ml). The organic phases were dried by means of diatomaceous earth (4 g) and approximately ⅓ of the solvent was evaporated in vacuo at a bath temperature of 40–45° C., the product starting to crystallize. After 10–15 hours at room temperature the product was filtered, washed with 2×50 ml of ethyl acetate and dried in vacuo at 50° C.

White to yellowish crystals were obtained (36 g, 53.7% yield based on penicillin G ester). The N,N-dimethylaniline contamination was 1100 ppm (GC-analysis).

The comparative example described above represents the non-continuous technique disclosed in SE patent No. 7810122-7, referred to in the opening part of the description. Although said Swedish patent discloses the use of an ion exchange resin to purify the product further, a comparison already here clearly shows the great advantages achieved by the new process according to the present invention.

Furthermore, neither of the ion exchange resin procedures described in said Swedish patent gives a degree of purity at the level obtained by the present invention. Irrespective of that, however, the novel process also means a non-obvious and much more advantageous alternative to the ion exchange technique from a process technological perspective, in addition to which the new process gives a very homogeneous, high quality product.

What is claimed is:

1. A process for purifying an ampicillin pro-drug ester of formula I:

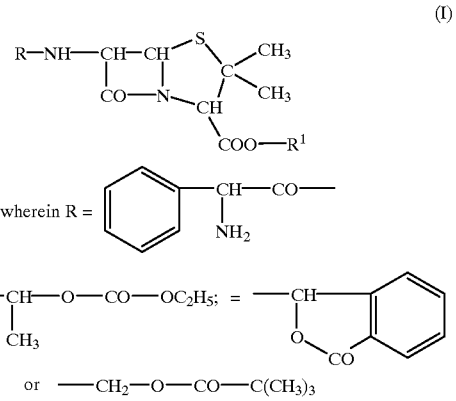

or an acid addition salt thereof;
from contaminants originating from the manufacture thereof, especially to remove base used when incorporating the R group into said ester of formula (I), such as from the corresponding ester wherein R is phenylacetyl, which comprises a step wherein a crude solution of said ampicillin pro-drug ester of formula (I), or an acid addition salt thereof, in an organic solvent therefor, is subjected to an evaporation which is controlled by the evaporation rate of the organic solvent such that a continuous operation is accomplished for the crystallization of the desired purified pro-drug ester, or salt thereof.

2. A process according to claim 1, wherein the continuous crystallization is performed at an evaporation rate corresponding to, per hour, 0.1–0.6 times the total volume of the added solution.

3. A process according to claim 1, wherein the continuous crystallization is performed at sub-atmospheric pressure.

4. A process according to claim 1, wherein the continuous crystallization is performed at a temperature within the range of 25–75° C.

5. A process according to claim 1, wherein said continuous crystallization operation is preceded by a step wherein the solution of said ester of formula (I), or acid addition salt thereof, is subjected to a step wherein polar contaminants are removed therefrom by an extraction with an aqueous phase.

6. A process according to claim 5, wherein said aqueous phase extraction step is performed continuously.

7. A process according to claim 6, wherein said continuous extraction step is performed in a counter current flow column.

8. A process according to claim 7, wherein the volume flow ratio of organic solution to aqueous extraction phase used is within the range of from 2:1 to 1:2.

9. A process according to any one of claims 5–8, wherein the medium used in said aqueous phase extraction comprises water containing an inorganic acid salt.

10. A process according to claim 9, wherein said medium contains 5–30% (w/w) of said salt.

11. A process according to claim 5, wherein the pH used in the aqueous phase extraction step is controlled within the range of 2–5.

12. A process according to claim 5, wherein said continuous crystallization operation is preceded by a step wherein the solution of said ester of formula (I), or acid addition salt thereof, is subjected to a step wherein organic contaminants are removed therefrom by an extraction with an organic phase.

13. A process according to claim 12, wherein said organic phase extraction step is performed continuously.

14. A process according to claim 12 or 13, wherein the organic solvent used in said organic phase extraction step is selected from butyl acetate, methyl isobutyl ketone and ethyl acetate, or mixtures thereof.

15. A process according to claim 12, wherein said aqueous phase extraction precedes said organic phase extraction.

16. A process according to claim 15, wherein an evaporation step is incorporated between said aqueous phase extraction step and said organic phase extraction step to evaporate organic solvent from the product-containing organic phase leaving said aqueous phase extraction, which organic solvent is then replaced by another organic solvent to be used in said organic phase extraction for the extraction of organic contaminants therein.

17. A process according to claim 15, wherein the aqueous phase which leaves the organic phase extraction step is subjected to a salting-out extraction step wherein the pro-drug ester to be crystallized is transferred from said aqueous phase into a new organic phase to be crystallized in said continuous crystallization operation.

18. A process according to claim 17, wherein the salting-out extraction step is performed continuously.

19. A process according to claim 17 or 18, wherein the salting-out extraction step is performed in the presence of an aqueous solution of an inorganic acid salt.

20. A process according to claim 19, wherein the organic solvent used in said salting-out extraction step is selected from butyl acetate, methyl isobutyl ketone, dichloromethane and ethyl acetate, or mixtures thereof.

21. A process according to claim 17, wherein the flow volume ratio of pro-drug ester solution:salt solution:organic solvent is within the range of 1.0–1.5:1.5–2.0:1.

22. A process for purifying a solution of an ampicillin pro-drug ester of formula I:

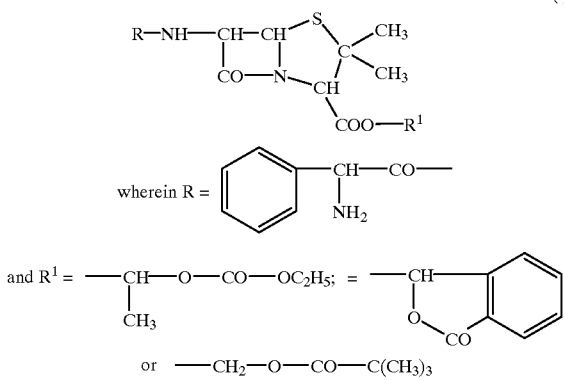 (I)

or an acid addition salt thereof;
from contaminants originating from the manufacture thereof, especially to remove base used when incorporating the R group into said ester of formula (I), such as from the corresponding ester wherein R is phenylacetyl, which comprises a step wherein a crude solution of said ampicillin pro-drug ester of formula (I), or an acid addition salt thereof, in an organic solvent therefor, is subjected to an extraction with an aqueous phase to remove polar contaminants therefrom, said extraction being performed continuously in a counter current flow column and with an aqueous medium containing an inorganic acid salt.

23. A process according to claim 22, wherein the volume flow ratio of organic solution to be purified to aqueous extraction phase used is within the range of from 2:1 to 1:2.

24. A process according to claim 22 or 23, wherein said medium contains 5–30% (w/w) of said salt.

25. A process according to claim 22, wherein the pH used in the aqueous phase extraction step is controlled within the range of 2–5.

26. A process according to claim 22, which is followed by a step wherein organic contaminants are removed by an extraction with an organic phase.

27. A process according to claim 26, wherein an evaporation step is incorporated between said aqueous phase extraction step and said organic phase extraction step to evaporate organic solvent from the product-containing organic phase leaving said aqueous phase extraction, which organic solvent is then replaced by another organic solvent to be used in said organic phase extraction for the extraction of organic contaminants therein.

28. A process according to claim 26 or 27, wherein said organic phase extraction step is followed by a salting-out extraction step wherein the pro-drug ester is transferred from said aqueous Phase into a new organic phase.

29. A process according to claim 22, which is followed by an evaporation step which is controlled by the evaporation rate of the organic solvent such that a continuous operation is accomplished for the crystallization of the desired purified pro-drug ester, or salt thereof.

30. A process according to claim 1 or 22, wherein the crude starting solution of ester of formula (I) in claim 1, or acid addition salt thereof, has been manufactured by incorporating the group R in said formula (I) into the 6-APA ester of formula (III):

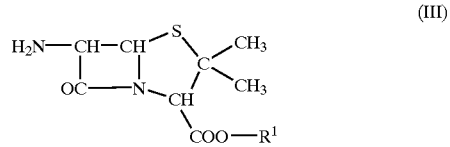 (III)

wherein $R^1$ is as defined in claim 1, in the presence of a base.

31. A process according to claim 1 or 21, wherein said ampicillin pro-drug ester of formula (I) is bacampicillin or an acid addition salt thereof.

32. A process according to claim 26, wherein the organic phase extraction is performed continuously.

33. A process according to claim 26 or 27, wherein the organic solvent used in the organic phase extraction is selected from butyl acetate, methyl isobutyl ketone and ethyl acetate, or mixtures thereof.

34. A process according to claim 28, wherein the salting-out extraction step is performed continuously.

35. A process according to claim 30, wherein the base is N,N-dimethylaniline and R is incorporated by means of phenylglycine chloride, or the hydrochloride thereof, as a reactant.

* * * * *